(12) United States Patent
Dimarzo et al.

(10) Patent No.: US 6,732,568 B2
(45) Date of Patent: May 11, 2004

(54) SENSOR PROBE FOR MEASURING TEMPERATURE AND LIQUID VOLUMETRIC FRACTION OF A LIQUID DROPLET LADEN HOT GAS AND METHOD OF USING SAME

(75) Inventors: Marino Dimarzo, Bethesda, MD (US); Paolo Ruffino, Mellingen (CH)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 10/465,614

(22) Filed: Jun. 20, 2003

(65) Prior Publication Data

US 2003/0209055 A1 Nov. 13, 2003

Related U.S. Application Data

(62) Division of application No. 10/103,561, filed on Mar. 22, 2002, now Pat. No. 6,609,412.
(60) Provisional application No. 60/277,772, filed on Mar. 22, 2001.

(51) Int. Cl.$^7$ ............................................. G01N 25/18
(52) U.S. Cl. ................... 73/25.01; 73/25.04; 73/29.01; 73/31.05; 73/61.43; 73/61.46
(58) Field of Search ................. 73/1.02, 1.06, 73/25.04, 25.01, 29.01, 31.05, 61.43, 61.46, 61.76, 61.77

(56) References Cited

U.S. PATENT DOCUMENTS

| | | | |
|---|---|---|---|
| 3,004,406 A | 10/1961 | Foote et al. | 62/373 |
| 3,011,336 A | 12/1961 | Weiss | 73/863.12 |
| 3,517,557 A | 6/1970 | Granger et al. | 73/863.12 |
| 3,548,607 A | 12/1970 | Pillsbury et al. | 62/50.1 |
| 3,630,496 A | 12/1971 | Hurst et al. | 261/26 |
| 3,751,660 A | 8/1973 | Thurston | 250/288 |
| 3,755,990 A | 9/1973 | Hardison | 95/223 |
| 3,878,690 A | 4/1975 | Bell et al. | 62/49.2 |
| 3,997,758 A | 12/1976 | Patel | 219/201 |
| 4,113,559 A | 9/1978 | Schweiger | 376/299 |
| 4,120,455 A | 10/1978 | Wilmotte et al. | 239/429 |
| 4,278,645 A | 7/1981 | Filss | 423/210 |
| 4,300,990 A | * 11/1981 | Maurer | 204/412 |

(List continued on next page.)

OTHER PUBLICATIONS

Walker, J. "Boiling Point and the Leidenfrost Effect", May 5, 2000, available on the Internet at ,http://www.wiley.com/college/phy/halliday320005/pdf/leidenfrost_essay.pdf>.*

(List continued on next page.)

*Primary Examiner*—Hezron Williams
*Assistant Examiner*—David A. Rogers
(74) *Attorney, Agent, or Firm*—Arent Fox Kintner Plotkin & Kahn, PLLC

(57) ABSTRACT

A sensor probe and method of use for determining the temperature, velocity, and/or liquid volumetric fraction of gas laden with droplets. In one variation, the probe includes a single heating element used in a well-characterized flow. The heating element is maintained above the Leidenfrost transition for the droplets, which prevents cooling effects from the droplets from impacting the temperature measurement. In another variation, the probe includes two or more heating elements arranged in similar flow environments. The property of interest is derived by relying on thermodynamic and heat transfer principles, which are not usable in conjunction with conventional devices. In one variation, the temperature is determined using a relationship function for characteristics of two heating elements, maintained at two different temperatures, along with the power needed to maintain constant temperature in each element, and by eliminating dependence on other variables for the determination, such as the velocity of the gas.

23 Claims, 9 Drawing Sheets

U.S. PATENT DOCUMENTS

| | | | |
|---|---|---|---|
| 4,358,343 A | 11/1982 | Goedde et al. | 201/1 |
| 4,370,154 A | 1/1983 | Namy et al. | 55/309 |
| 4,726,194 A | 2/1988 | Mackay et al. | 62/50.1 |
| 4,756,200 A | 7/1988 | Ramsner et al. | 73/863.11 |
| 4,804,167 A | 2/1989 | Kock et al. | 266/186 |
| 4,814,612 A | 3/1989 | Vestal et al. | 250/288 |
| 4,944,035 A | 7/1990 | Aagardl et al. | 702/136 |
| 4,956,793 A | 9/1990 | Bonne et al. | 702/50 |
| 4,960,992 A | 10/1990 | Vestal et al. | 250/288 |
| 5,038,304 A | 8/1991 | Bonne | 702/99 |
| 5,348,394 A | 9/1994 | Hori et al. | 374/44 |
| 5,362,031 A | 11/1994 | Heilmann et al. | 266/69 |
| 5,603,984 A | 2/1997 | Keim et al. | 427/133 |
| 5,974,822 A | 11/1999 | Kopko | 62/310 |
| 5,992,159 A | 11/1999 | Edwards et al. | 62/64 |
| 6,190,039 B1 * | 2/2001 | Yaguchi | 374/164 |
| 6,216,485 B1 | 4/2001 | Kramer et al. | 62/374 |

OTHER PUBLICATIONS

Schmehl et al., "CFD Analysis of Spray Propagation and Evaporation Including Wall Film Formation and Spray/Film Interactions", pp. 1–11.

Wang et al., "Mist/Steam Cooling for Advanced Turbine Systems", pp. 1–15.

Lee et al., "Development of a New Model and Heat Transfer Analysis of Impinging Diesel Sprays on a Wall", pp. 1–26, Published in Atomization and Sprays, vol. 11, pp. 85–105, 2001.

* cited by examiner ations Ser. No. 10/103,561, now U.S. Pat. No. 6,609,412 filed Mar. 22, 2002, which claims benefit of U.S. Provisional Application No. 60/277,772 filed Mar. 22, 2001. The disclosures of the prior application are hereby incorporated by reference herein in their entirety.

SENSOR PROBE FOR MEASURING TEMPERATURE AND LIQUID VOLUMETRIC FRACTION OF A LIQUID DROPLET LADEN HOT GAS AND METHOD OF USING SAME

CROSS-REFERENCE TO RELATED APPLICATIONS

This is a division of application Ser. No. 10/103,561, now U.S. Pat. No. 6,609,412 filed Mar. 22, 2002, which claims benefit of U.S. Provisional Application No. 60/277,772 filed Mar. 22, 2001. The disclosures of the prior application are hereby incorporated by reference herein in their entirety.

BACKGROUND OF THE INVENTION

1. Field of the Invention

The invention relates generally to a wet gas probe. More particularly, this invention relates to a sensor probe capable of accurately measuring the temperature and liquid volumetric fraction of a hot gas laden with liquid droplets.

2. Description of Related Art

For many liquids, there is a temperature well above the boiling point called the Leidenfrost point or Leidenfrost transition. As an example, water has a Leidenfrost point of 300–350° C. at atmospheric conditions. Consider a simple experiment where a droplet of water is placed on a surface kept at a temperature above the boiling point of water. If the temperature of the surface is below the Leidenfrost point, then the droplet starts to spread out and vaporizes rather quickly.

However, if the temperature of the surface is at or above the Leidenfrost point, the bottom layer of the droplet vaporizes almost immediately on contact, creating a cushion of vapor that repels the rest of the droplet from the surface. Furthermore, the evaporation of the bottom layer of the droplet from the surface produces a cooling effect, which detrimentally affects the heating of the surface. The remaining portion of the droplet does not make contact with the surface, and thus no heat can be transferred directly from the surface to the droplet. At such high temperatures, one might expect that the vapor layer would quickly transfer enough heat to the rest of the droplet to vaporize the droplet. Water vapor, however, is a very poor conductor of heat at these temperatures. Hence, the vapor layer actually acts as an insulator.

Currently it is quite difficult to accurately measure gas temperature in a liquid droplet and gas mixture. Most common gas measurement devices, such as thermocouples and resistance temperature detectors (RTD), work on the principal that the electrical resistance of most materials varies with temperature. Hence, knowledge of the functional relationship between temperature and change in resistance of a given material(s) and measurement of this change allows for inference of the temperature of the gas stream. Generally, these devices are comprised of different metals, which have high thermal conductivity. In a liquid-droplet gas mixture, the droplets will tend to impact and coat the surface of these devices. The liquid on the surface of the probe draws heat from the measurement device, in a process known as evaporative cooling. This process results in measurement of temperatures much below the true gas temperature. This phenomenon prevents these common temperature measurement devices from accurately measuring gas temperature in this environment. As described above, the invention eliminates this problem by preventing the droplet from impacting the surface of the probe by keeping the measurement surface above the Leidenfrost point.

The above-identified phenomena give rise to an unsolved problem in the prior art of measuring the temperature and other characteristics of gases laden with liquid droplets. The need to solve this problem arises in a wide variety of contexts, including, for example, measurement of gas temperature in propulsion and power generation systems, which often use water or other liquid introduced into the system to, for example, control emissions (e.g., pollution control) or augment power. In such applications, determination and control of gas temperature may be important to performance. Many other systems, devices, and situations arise, such as a gas turbine, combustion engine, tank, pipe, duct, manifold, chamber, or the like, as well as external flows, including, for example, droplets in an open air environment, in which the presence of liquid droplets in a gas can produce difficulties in measuring gas temperature and other properties of the gas.

As an example, one simple conventional temperature and liquid sensitive system for which this problem can arise is a fire detection system, an example of application of which is as follows. As is well known, fire detection systems are installed in residential and commercial buildings to protect property and occupants from fire. An important characteristic of the fire detection system is the capability to detect a fire in the early stages, when the fire is still small. Early detection and activation by fire suppression devices are important to allow more time for the evacuation of the occupants as well as to increase the chance of successfully suppressing the fire before extensive damage is caused to the buildings. Therefore, the early detection of a fire is very important.

Ceiling mounted devices that do not interfere with normal room arrangements are generally preferred for fire protection purposes. Automatic sprinklers are devices that distribute water onto a fire in sufficient quantity either to extinguish the fire in its entirety or to prevent the spread of the fire in case the fire is too far from the water discharged by the sprinklers. Typically, the water is fed to the sprinklers through a system of piping, suspended from the ceiling, with the sprinklers placed at regular intervals along the pipes. The orifice of the sprinkler head is normally closed by a disk or cap held in place by a temperature sensitive releasing element. The temperature sensitive releasing element of the sprinkler will be referred to hereinafter as a sprinkler link.

Automatic sprinklers have several temperature ratings that are based on standardized tests in which a sprinkler is immersed in a liquid and the temperature of the liquid raised very slowly until the sprinkler activates. The temperature rating of most automatic sprinklers is stamped on the sprinkler. The time delay between the onset of the fire and the activation of the sprinkler depends upon several parameters, such as the placement of the sprinkler with respect to the fire, the dimensions of the enclosed space, the energy generated by the combustion and the sensitivity of the sprinkler.

Buoyancy pushes the hot products generated by a fire toward the ceiling while mixing with room air to form a hot-gas plume. Impingement of the hot-gas plume on the ceiling results in a gas flow near the ceiling, even at a considerable distance from the core of the fire. This flow is responsible for directing hot gases to the thermally actuated fire detection devices.

The rate of heat released by the fire and the room dimensions are the main parameters of considerable importance in any discussion of fire-induced convection near the room ceiling. Also, the size and the composition of the sprinkler link influences the sensitivity of the sprinkler. Other conditions being equal, the sensitivity of a sprinkler is inversely proportional to the time required for the sprinkler link to melt. Therefore, sprinklers are rated according to their Response Time Index, hereinafter referred to as RTI, which characterizes the speed of the sprinklers response to a fire.

The RTI is the product of the thermal time constant of the sprinkler link and the square root of the flow velocity of the hot gas. This parameter is reasonably constant for any given sprinkler and is considered sufficient for predicting the sprinkler response for known gas temperatures and velocities near the sprinkler. However, recent full-scale tests on warehouse fires uncovered a behavior of sprinklers that does not correspond to the predictions of the RTI model.

The RTI model considers the sprinkler link as a cylinder in cross-flow. It is assumed that the heat transfer between the hot gases flowing under the ceiling and the sprinkler is convective and radiative, thus, among other factors, the RTI model neglects the presence of water droplets in the airflow.

The first sprinkler to activate in case of fire is referred to as a primary sprinkler and the surrounding sprinklers are identified as secondary sprinklers. Tests show that the primary sprinkler activates as predicted, but the secondary sprinklers respond after a much longer delay than suggested by the RTI model. In some cases, the sprinklers immediately surrounding the primary sprinkler do not activate at all, whereas the sprinklers farther away do activate.

Such observations may be explained in part by considering the presence of water droplets in the hot gas plume following the activation of the primary sprinkler. Some of the water droplets sprayed by the primary sprinkler do not reach the ground but are entrained and carried away by the ascending plume. Most of these water droplets evaporate inside the plume, while a small fraction of the remaining water droplets travel far enough to reach and impact the secondary sprinklers. The subsequent evaporation of the water droplets from the sprinkler link surface of the secondary sprinklers produces a cooling effect, which delays the heating of the sprinkler link. The delay in the heating of the sprinkler link results in a delay in the activation of the sprinkler which cannot be predicted by the RTI model.

There remains an unmet need to solve the problem of measurement of the characteristics, including gas temperature, for hot gases containing liquid droplets in a wide range of environments and applications.

SUMMARY OF THE INVENTION

The present invention solves these and other problems of the prior art by providing a sensor probe and method of use for determining the temperature and liquid volumetric fraction of a hot gas laden with liquid droplets in a wide range of applications. In one embodiment, a single heating element is used in a well-characterized, droplet-laden flow. The heating element is maintained above the Leidenfrost transition for the droplets which prevents cooling effects from the droplets from impacting the temperature measurement. In this embodiment, the heat loss from the probe is determined by the power needed to maintain a constant temperature in the element and the convective heat transfer coefficient is determined by calibration in the well-characterized flow or from fundamental properties of the well-characterized flow. Specifically, if the Reynolds number (Re) and the Prandtl number (Pr) of the flow are known, the convective heat transfer coefficient can be calculated from the Nusselt (Nu) number by a person skilled in the art. Similarly, if the temperature of the flow is known, the velocity of the flow can be determined through the velocity dependence of the convective heat transfer coefficient by calibration or from fundamental properties of the fluid. Such determination can include, but is not limited to, use of a processor, such as a personal computer, minicomputer, main frame computer, or microcomputer.

In another embodiment of the present invention, the heating elements are arranged so as to be in similar flow environments, such as by being arranged parallel, coplanar, or coaxial to one another. For example, in a single direction flow environment, the heating elements may be arranged coaxial to one another, perpendicular to the direction of flow. At least two heating elements are maintained at a temperature above the Leidenfrost transition for the liquid droplets (e.g., the Leidenfrost transition for water droplets is in a range between 300–350° C. at atmospheric conditions; other liquids have determinable Leidenfrost transition temperature ranges), which prevents cooling effects of the droplets from impacting the temperature measurement. The gas temperature is derived by relying on thermodynamic and heat transfer principles, which are not usable in conjunction with conventional devices (e.g., devices designed for use at below Leidenfrost transition temperatures and for which the presence of liquid droplets impacts performance). In one variation, the temperature is determined using a relationship function for characteristics of two heating elements, maintained at two different temperatures, and the power needed to maintain a constant temperature in each element, and by eliminating dependence on other variables for the determination, such as the velocity of the gas, one important factor is heat loss from the heating elements.

More specifically, in an embodiment of the present invention, a temperature of the hot gas laden within liquid droplets is determined based on characteristics of heating elements in the hot gas and liquid droplet environment, such as by using a derived relationship function for the first and second temperatures of first and second heating elements positioned so as to be in a similar flow environment. Heat loss for the two elements is usable in this embodiment to determine gas properties, such as gas temperature. Heat loss can be measured in many ways. For example, if the heating elements are maintained at a constant temperature using a power source, heat loss varies as a function of the power supplied to each element, and the ratio of power supplied to the first and second heating elements by the controller is usable to determine relative heat loss, and from this information, gas temperature can be determined. As the derived relationship function eliminates variables for gas velocity, the determination of temperature is not affected by the velocity of the hot gas flow, and as the heating elements are both maintained above the Leidenfrost point for the liquid present in the hot gas, the presence of the liquid droplets in the hot gas flow likewise does not affect temperature determination.

In one embodiment of the present invention, heat loss is determined based on the power needed to maintain each heating element at a predetermined temperature, with the heat loss of the first and second heating elements and ratio of power supplied to the first and second heating elements being used to determine the temperature of the hot gas laden with liquid droplets, based on the relationship of $T_G = A \cdot w + B$, where $T_G$ is the temperature of the hot gas, A and B are numerical constants having values dependent upon the configuration of the sensor probes, and w is the ratio of an electrical resistance across the second heating element at the second temperature to an electrical resistance across a resistor that is in series with the second heating element.

According to yet another aspect of the invention, a liquid volumetric fraction of the hot gas laden with liquid droplets is determinable using information obtained from one or more of the heat elements and information obtained from a wetted sensor. In one embodiment, the liquid volumetric fraction of the hot gas is determined based on the relationship of $\beta=(0.012\pm0.001)(T_G-T_W)/(U\cdot D)^{1/2}$, where $\beta$ represents the liquid volumetric fraction, $T_G$ is the temperature of the hot gas laden with liquid droplets, $T_W$ is a temperature measured by a wetted sensor, U is the velocity of the hot gas laden with liquid droplets, and D is the outer diameter of the wetted sensor.

In one embodiment of the present invention, the controller controls the operation parameters of the first and second heating elements simultaneously (i.e., at the same time), using, for example, a circuit containing a Wheatstone bridge.

In an embodiment of the present invention, the sensor includes at least two heating elements connected to insulating rods attached to a support frame. A controller is connected to the support frame and controls the operation parameters of each of the heating elements, including the temperature of the heating elements. The first heating element is configured to be maintained at a first temperature and the second heating element is configured to be maintained at a second temperature that is less than the first temperature. The first and second temperatures are both above a Leidenfrost transition temperature at atmospheric conditions for the liquid present in the gas.

In an embodiment of the present invention, the first and second heating elements may be any of a wide variety of shapes, including cylindrical, spherical, or having a rectangular or trapezoidal cross-section, and may be, effectively, one, two, or three dimensional structures.

In one embodiment of the present invention for use in generally single directional gas flow applications, the first and second heating elements are arranged to be parallel relative to each other. An insulator is connected to each of the first and second heating elements that may be comprised of a rigid ceramic assembly. In another embodiment of the present invention for generally single directional gas flow applications, the first and second heating elements are arranged to be coaxial relative to each other. In this embodiment, a support frame is used that includes three bent rods connected at a first end of each rod and equidistant from each other at a second end of each rod. The second ends of the rods are provided on a line coaxial with the longitudinal axes of the first and second heating elements. A distance between the second ends of the rods is then equal to the length of the first and second heating elements.

A wide range of other configurations of the first and second heating elements are also usable in conjunction with the present invention, so long as each element is positioned in a similar flow environment (e.g., so that similar convective heat transfer error occurs for each element).

In an embodiment of the present invention, a connector may connect the first and second heating elements to the second ends of the rods. The connector may comprise a bore formed in the second end of each rod and a fastener having a threaded portion and a head portion. The bore can be sized and configured to receive the threaded portion of the fastener and the head portion of the fastener maintains the heating element against the corresponding rod. The fastener may also include a clamp having a bore identical to the bore in the second end of each rod and a terminal that maintains a predetermined distance between the clamp and rod. The bores can be sized and configured to receive the threaded portion of the fastener and the clamp maintains the heating element against the corresponding rod.

According to yet another aspect of the invention, the first and second heating elements may comprise a platinum wire. Furthermore, the support frame and connecting rods can be enclosed within temperature-shrinking tubing.

In another aspect of the invention, a method of measuring characteristics of a hot gas laden with liquid droplets uses a sensor probe having at least two heating elements. In one embodiment, each heating element is connected in series with an insulator and a support frame, and the insulator connected to each heating element is, in turn, connected to a support frame. A controller controls the temperature of each of the heating elements. A first heating element is configured to be maintained at a first temperature and a second heating element is configured to be maintained at a second temperature that is less than the first temperature, with both the first temperature and the second temperature being above the Leidenfrost temperature for the liquid present in the gas.

The method includes positioning the first and second heating elements in a flow of hot gas laden with liquid droplets, the elements being positioned in a similar flow environment, such as placement in parallel or coaxial, and orthogonal to the direction of the hot gas if the gas has a generally single flow direction. In one embodiment, power is then supplied from the controller to the first and second heating elements and the first and second temperatures are maintained above a Leidenfrost transition temperature for the liquid at atmospheric conditions. A temperature of the hot gas laden within liquid droplets is then determined, based on a relationship between a function of the first and second temperatures of the first and second heating elements and the power supplied to the first and second heating elements.

According to another aspect of the invention, the method also includes determining the temperature of the hot gas laden with liquid droplets based on the relationship of $T_G=A\cdot w+B$, where $T_G$ is the temperature of the hot gas, A and B are numerical constants having values dependent upon the configuration of the sensor probe, and w is the ratio of an electrical resistance across the second heating element at the second temperature and an electrical resistance across a resistor in series with the second heating element.

According to another aspect of the invention, the method also includes determining a liquid volumetric fraction of the hot gas laden based on the relationship of $\beta=(0.012\pm0.001)(T_G-T_W)/(U\cdot D)^{1/2}$ where $\beta$ represents a liquid volumetric fraction, $T_G$ is a temperature of the hot gas laden with liquid droplets, $T_W$ is a temperature measured by a wetted sensor, U is a velocity of the hot gas laden with liquid droplets, and D is an outer diameter of the wetted sensor.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DETAILED DESCRIPTION OF THE PREFERRED EMBODIMENTS

Figure 1:
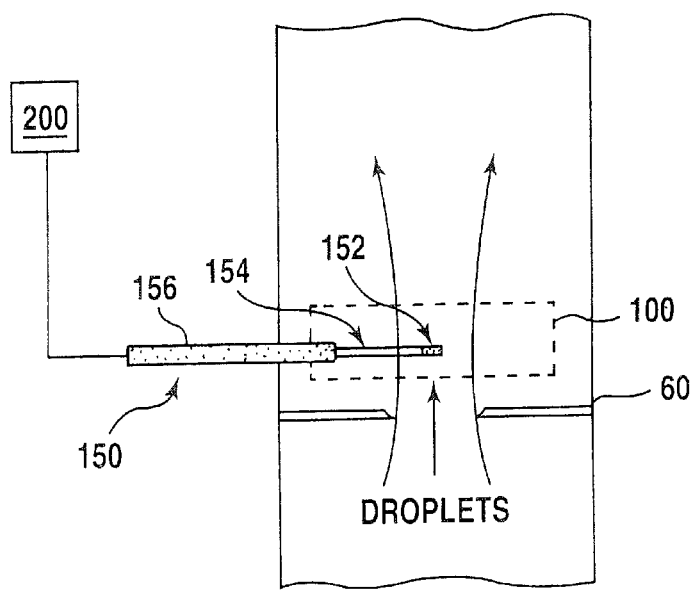
FIG. 1 is a schematic drawing indicating the positioning of an example sensor probe in the center of a test section, in accordance with an embodiment of the present invention.

The present invention provides a sensor probe and method of use for determining the temperature and liquid volumetric fraction of a hot gas laden with liquid droplets in a wide range of applications. In one embodiment, a single heating element is used in a well-characterized, droplet-laden flow. The heating element is maintained above the Leidenfrost transition for the droplets which prevents cooling effects from the droplets from impacting the temperature measurement. In this embodiment, the heat loss from the probe is determined by the power needed to maintain a constant temperature in the element and the convective heat transfer coefficient is determined by calibration in the well-characterized flow or from fundamental properties of the well-characterized flow. Specifically, if the Reynolds number (Re) and the Prandtl number (Pr) of the flow are known, the convective heat transfer coefficient can be calculated from the Nusselt (Nu) number by a person skilled in the art. Similarly, if the temperature of the flow is known, the velocity of the flow can be determined through the velocity dependence of the convective heat transfer coefficient by calibration or from fundamental properties of the fluid. Such determination can include, but is not limited to, use of a processor, such as a personal computer, minicomputer, main frame computer, or microcomputer.

In another embodiment of the present invention, the probe includes two or more heating elements arranged so as to be in similar flow environments. The two heating elements are maintained at a temperature above the Leidenfrost transition for the liquid droplets, which prevents cooling effects of the droplets from impacting the temperature measurement. The gas temperature is derived by relying on thermodynamic and heat transfer principles, which are not usable in conjunction with conventional devices (e.g., devices designed for use at below Leidenfrost transition temperatures). In one variation, the temperature is determined using a relationship function for characteristics of two heating elements, maintained at two different temperatures, along with the power needed to maintain a constant temperature in each element, and by eliminating dependence on other variables for the determination, such as the velocity of the gas.

Analysis of data for conventional measurement techniques and consideration of the properties of hot gas and liquid droplets are useful in identifying relationships among probes that allow determination of temperature and other characteristics of hot gases containing liquid droplets. Conventional measurement of gas temperature in wet and dry conditions and some properties of the gas and liquid droplets, as well as devices relating to such measurement is described further below in conjunction with FIGS. 10–13.

Turning now to the invention of this application, two temperature properties can be measured in a hot gas laden with liquid droplets, using two or more probes, which are referred to herein as cold and hot heating elements. The relationship between the temperature properties is usable to determine the gas temperature, as will be explained further below.

From Newton's law of convection, the following can be written for the cold and hot heating elements, respectively:

$$Q_H = h_H \cdot S \cdot (T_H - T_G) \quad (1)$$

$$Q_C = h_C \cdot S \cdot (T_C - T_G) \quad (2)$$

Dividing Equation (1) by Equation (2) (note that $Q_C$ is always different from zero since the temperature of cold heating element is greater than any contemplated gas temperature), results in the following expression:

$$\frac{Q_H}{Q_C} = \frac{h_H}{h_C} \cdot \frac{T_H - T_G}{T_C - T_G} \quad (3)$$

Although Equation (3) is theoretically correct, it does not match very well with preliminary test results gathered from actual experiments, most likely due to the fact that convection is not the only heat transfer mechanism involved in the measurement, though the most significant.

The gas temperature is obtained by considering the relationships among the hot heating element temperature $T_H$ and its power $Q_H$, the cold heating element temperature $T_C$ and its power $Q_C$, and the actual gas temperature $T_G$, which corresponds to zero heating element power.

From these three conditions and again from the expressions of heat transfer, the following relationship is obtained for air laden with liquid droplets:

$$\frac{T_H - T_G}{T_C - T_G} = F \cdot \left(\frac{Q_H}{Q_C}\right)^b \quad (4)$$

where F is a coefficient that depends on the ratio of the heat transfer coefficients.

Experimental tests performed at gas temperatures ranging between 100 and 250° C. have shown that the value of F is very close to 0.9. The exponent b would be expected to be almost equal to unity if the heat transfer mechanism were only convective. In such a case, Equation (4) reduces to Equation (3). But, since it is believed that radiation could play a small, but not negligible, role in this configuration, the exponent b is introduced as a parameter in Equation (4). The exponent b has been experimentally found to be indeed smaller than one in some applications, due to the relation between the heat flux dissipated by the heating element and the temperature of the heating element itself. However, the effect of radiation can be eliminated in some cases by, for example, using a different orientation of the heating elements.

In Equation (4), the hot and cold heating element temperatures, $T_H$ and $T_C$, are known because they are set by the operator and electronically controlled by, for example, a controller. The powers $Q_H$ and $Q_C$ are easily obtained from the formula $Q=i^2R$ (assuming power is provided via an electrical circuit), where i is the quadratic mean value of the current flowing into the heating element and R is the resistance of the heating element. The resistance of each heating element is measured by changing the temperature in a predetermined range, such as 100–900° C., and performing a measurement at intervals, such as every 100° C. For example, the analysis of the experimental data may show that the resistance according to an embodiment of the present invention using example heating elements produces an average resistance value of 112Ω and ranges from 100Ω at 100° C. to 124Ω at 900° C. The current i is measured with appropriate instrumentation readily available in the market.

Therefore, Equation (4) can be rearranged in the following way:

$$\frac{T_H - T_G}{T_C - T_G} = F \left( \frac{i_H^2 \cdot R_H}{i_C^2 \cdot R_C} \right)^b = F \cdot \left( \frac{R_H}{R_C} \right)^b \left( \frac{i_H}{i_C} \right)^{2b} \quad (5)$$

The quantities F' and b' may be defined as follows:

$$F' = F \cdot \left( \frac{R_H}{R_C} \right)^b \quad (6,7)$$

$$b' = 2b$$

It is thus possible to rewrite Equation (4) in a substantially similar way:

$$\frac{T_H - T_G}{T_C - T_G} = F' \left( \frac{i_H}{i_C} \right)^{b'} \quad (8)$$

Since the resistance of the heating elements increases with the temperature (assuming an electrical circuit for the heating elements), the ratio $R_H/R_C$ is somewhat larger than the unity. This implies that F' is even closer to the unity than F, thus simplifying considerably the analysis of the data.

Several experiments were performed using the first embodiment of the sensor probe and Equation (8). A series of tests were used to evaluate the coefficient F' and b' wherein it was found that F'≈0.9 and b'≈1.7.

The heating elements of the sensor probe output a heat power Q, which obeys the Newton's law of convection. Therefore, one can obtain the convective heat transfer by dividing the heat power Q by a product of the surface area of the heating element and the temperature difference between the heating element and gas. The velocity is then obtained through correlations for the Nusselt number versus the available Reynolds number.

Use of these relationships for determining gas temperature will now be demonstrated using an example application of the present invention in a simple gas flow environment. It will be readily apparent to those skilled in the art that other techniques for measuring heat loss for sensors maintained above the Leidenfrost temperature may be used in conjunction with the present invention, and that gas temperature and other properties may be similarly determined in many other, more complex environments, so long, for example, as each of the probes is located in a similar flow environment or accounting is made for differences in flow environment.

FIG. 1 is a schematic drawing indicating the positioning of an example sensor probe 150, in accordance with an embodiment of the present invention, located in the center of a test section 100. In the illustrated embodiment, the sensor probe 150 is cylindrical, however, it is within the scope of this invention to have the sensor probe be any suitable geometry, such as spherical, oblong, oval, box-shaped, rectangular, square, trapezoidal, pyramid shaped, as well as a plate or a disc shape, or a shape of a wire.

In the illustrated exemplary embodiment of FIG. 1, the sensor probe 150 includes a heating element 152 placed in series with a rigid insulator 154, preferably made of ceramic, which minimizes heat losses to a support 156 connected thereto.

It should be noted that reference number 152 is used when discussing the characteristics and features of the heating elements in general and the heating elements are identified as having subscripts H and C when discussing the particular features or relationships of and between, for example only, a hot temperature heating element $152_H$ and a cold temperature heating element $152_C$.

The gas temperature $T_G$ is obtained based on the measurements of two heating elements $152_H$ and $152_C$ maintained at a hot temperature and a cold temperature $T_H$ and $T_C$, respectively, by a controller 200. The hot and cold temperatures $T_H$ and $T_C$ of the heating elements $152_H$ and $152_C$ are above the Leidenfrost transition and thus unaffected by the liquid droplets present in the hot gas flow. For purposes of this example only, water was the liquid forming the droplets. Calculations reveal the temperature of the gas $T_G$ is a function of the hot and cold temperatures $T_H$ and $T_C$ of the heating elements $152_H$ and $152_C$, respectively, and the ratio of the power supplied thereto by the controller 200.

To demonstrate the concept, consider a heating element 152 immersed in a gas kept at constant temperature and flowing at constant velocity over the heating element. The measurement of the power supplied thereto is a function of the temperature of the heating element 152. In dry conditions, the power supply from the controller 200 is linearly proportional to the temperature. This is under the assumption that the heat transfer coefficient does not change significantly with the temperature of the heating element 152 and that the temperature of the heating element 152 is not too high such that the radiative contribution can be neglected.

When liquid droplets are present, the linear dependence is accurate if the temperature of the heating element 152 is above the Leidenfrost transition. For liquid water in this example, the transition occurs approximately at 300–350° C. at atmospheric conditions. The power dissipated by the heating element 152 under wet conditions deviates from the linear behavior below that temperature because the heating element 152 can also supply the energy to vaporize the water droplets deposited on its surface.

It should be noted that recent studies indicate that neither the velocity of the liquid droplets nor the impact frequency of liquid droplets over a hot surface significantly influence the Leidenfrost transition.

Figure 2:
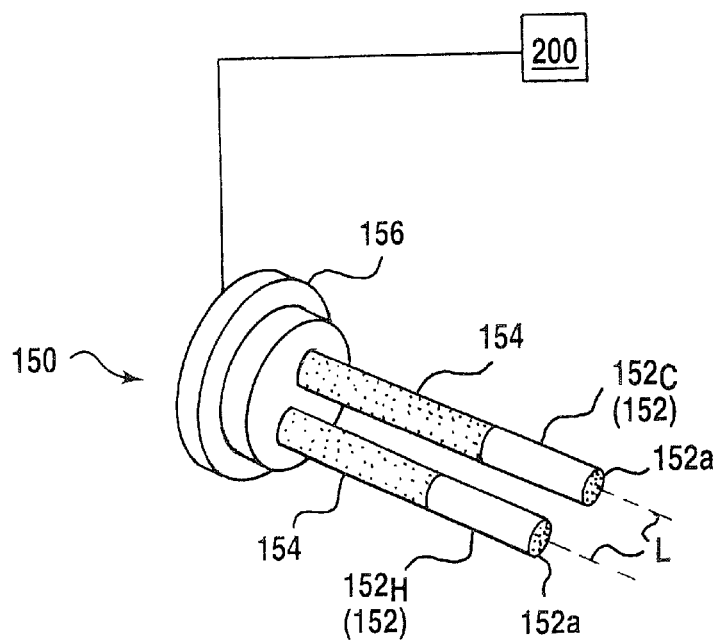
FIG. 2 shows a dual heating element sensor probe according to a first embodiment of the invention.

FIG. 2 illustrates one embodiment of the dual heating element sensor probe 150 of the present invention. The sensor probe 150 of this embodiment is designed to measure the temperature of a one-dimensional stream of hot gas with a velocity orthogonal to a plane of the probe having the longitudinal axes L of the two heating elements $152_H$ and $152_C$. Whether the sensor probe 150 is of this or another geometric configuration, the critical requirement is that it is placed so that each heating element is located in a similar flow environment.

The heating elements 152 are controlled, preferably at the same time (i.e., simultaneously) by the controller 200. It should be noted that the specific details of the controller 200 are not relevant to an understanding of this invention. Rather, in this embodiment, the controller 200 need only be able to maintain the two heating elements $152_H$ and $152_C$ at different temperatures, that is, a hot temperature $T_H$ and a cold temperature $T_C$, respectively, where $T_H>T_C$.

As indicated above, the heating elements $152_H$ and $152_C$ used in the first embodiment of the sensor probe 150 output a heat power Q, which obeys the Newton's law of convection. Therefore, one can obtain the convective heat transfer by dividing the heat power Q by a product of the surface area of the heating element 152 and the temperature difference between the heating element and gas. The velocity of the gas is then obtained through correlations for the Nusselt number versus the available Reynolds number. For a 9.3 mm diameter cylinder in cross-flow, the Reynolds number ranges from 600 to 2000. The heating element 152 is maintained at a relatively low temperature, such as, for example, 400° C., to avoid significant heat transfer by radiation.

A second embodiment of the sensor probe 250 includes a smaller size of the two heating elements $252_H$ (252) and $252_C$ (252) and significantly improves the operation of the sensor probe 250 and reduces the amount of error in the measurement. In particular, by rearranging the two heating elements $252_H$ and $252_C$ to be coaxial or in-line eliminates any radiative heat transfer between the two heating elements. Furthermore, reducing the diameter of the heating elements $252_H$ and $252_C$ lowers the heat transfer to the surroundings.

The lower heat transfer to the surroundings by the heating elements $252_H$ and $252_C$ of this second embodiment is because the radiative heat power $Q_{rad}$ depends linearly on the diameter of the heating elements 252 and the convective heat power $Q_{conv}$ depends on the square root of the diameter. Hence, the convective heat transfer will decrease less than the radiative heat transfer if a smaller diameter of the heating elements 252 is used.

The second embodiment of the sensor probe 250 results in a more flexible and effective geometry that enables measurement of gas temperature for flows orthogonal to the longitudinal axis LL of the sensor probe. Furthermore, the approach of the gas flow to the sensor probe 250 can be from anywhere within 360° of a plane orthogonal to longitudinal axis LL of the heating elements $252_H$ and $252_C$. Also, the diameter of the heating elements 252 is reduced to 0.2 mm.

The second embodiment of the sensor probe 250 provides many other advantages. For example, the elimination of heating element-to-heating element radiative exchanges that are present in the first embodiment. Also, the influence of the liquid droplets over the heat transfer between cylindrical outer surface and the hot gas is reduced. The radiative heat transfer to the suroundings is also reduced. Furthermore, the response time of the sensor probe 250 is reduced from several minutes for the first embodiment to a few seconds for the second embodiment.

Figure 3:
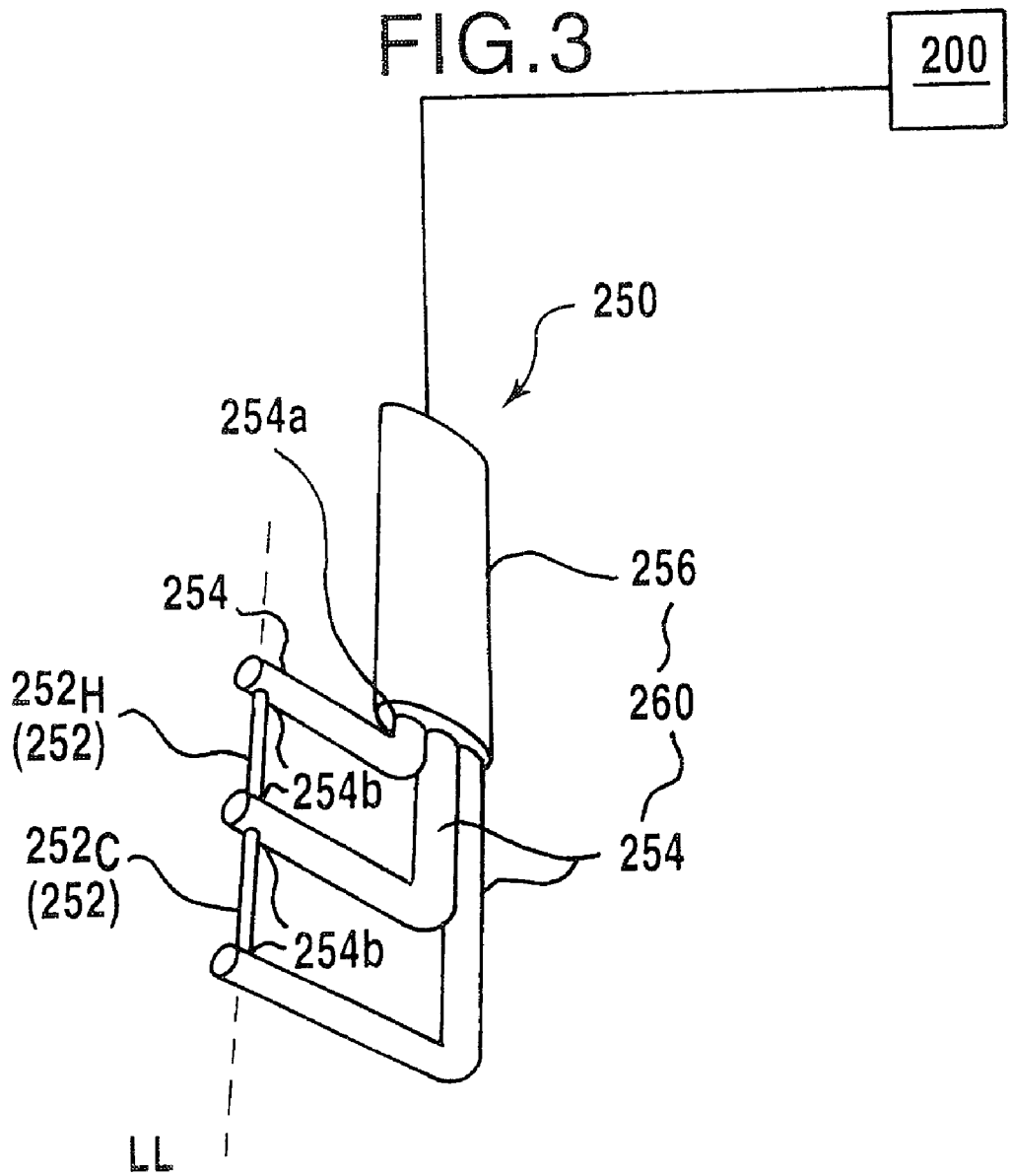
FIG. 3 shows a dual heating element sensor probe according to a second embodiment of the invention.

As shown in FIG. 3, the sensor probe 250 according to the second embodiment preferably includes a support frame 260 and a pair of identical heating elements $252_H$ and $252_C$ (252). The support frame 260 includes three rods 254, preferably made from copper, that are curved and joined at a first end 254a wherein the rods 254 are equidistant from each other at a second end 254b. The spacing between the second ends 254b of the rods 254 is equal to the length of the heating elements 252, which, in the embodiment illustrated in FIG. 3 are preferably made of 0.2 mm diameter platinum wire having a length of approximately 30 mm. However, as stated above, the sensor probes 150 and 250 may be of any suitable geometric configuration, such as a sphere, disc, rectangle, and the like. Therefore, the spacing between the second ends 254b of the rods 254 should be able to receive and hold therebetween two identical heating elements, regardless of the geometric configuration of the heating elements.

In the exemplary embodiment illustrated in FIG. 3, in order to have negligible electrical resistance between the two heating elements $252_H$ and $252_C$, which comprise platinum wires, respectively, the rods 254 should have a rather large diameter, such as, for example only, 6.4 mm. It should be understood that the diameter of the rods 254 will change depending on the material, geometric configuration, size, length, diameter, and other such relevant characteristics of the material chosen to comprise the heating elements 252. Preferably, temperature-shrinking tubing 255 could be used to insulate the rods 254 from each other.

Figure 4:
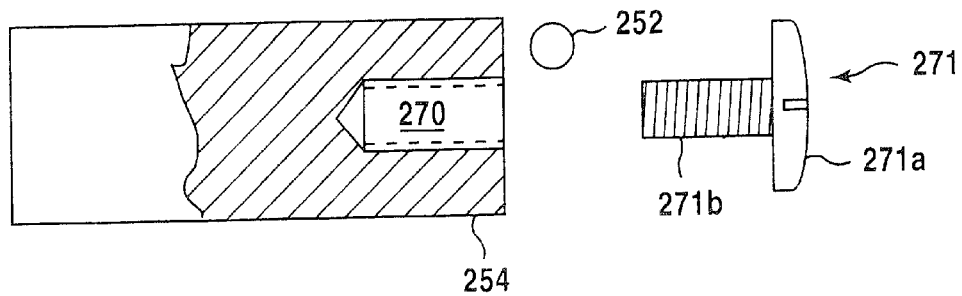
FIG. 4 illustrates an example of how the heating elements of the sensor probe are attached to rods.

In embodiments of the present invention, the heating elements 252 are attached to the second ends 254b of the three rods 254. FIG. 4 illustrates one example of how the heating elements 252 can be attached to the rods 254. For example, each rod 254 could have a bore 270 formed therein that is sized and configured to receive a fastening device 271, which is shown as a screw, but can be any known or later developed suitable fastening device. When the threaded portion 271b of the fastening device 271 is threadably inserted into the bore 270 of the rod 254, the head portion 271a of the fastening device 271 would clamp the heating element 252 between a bottom surface of the head portion 271a and the body of the rod 254.

Figure 5:
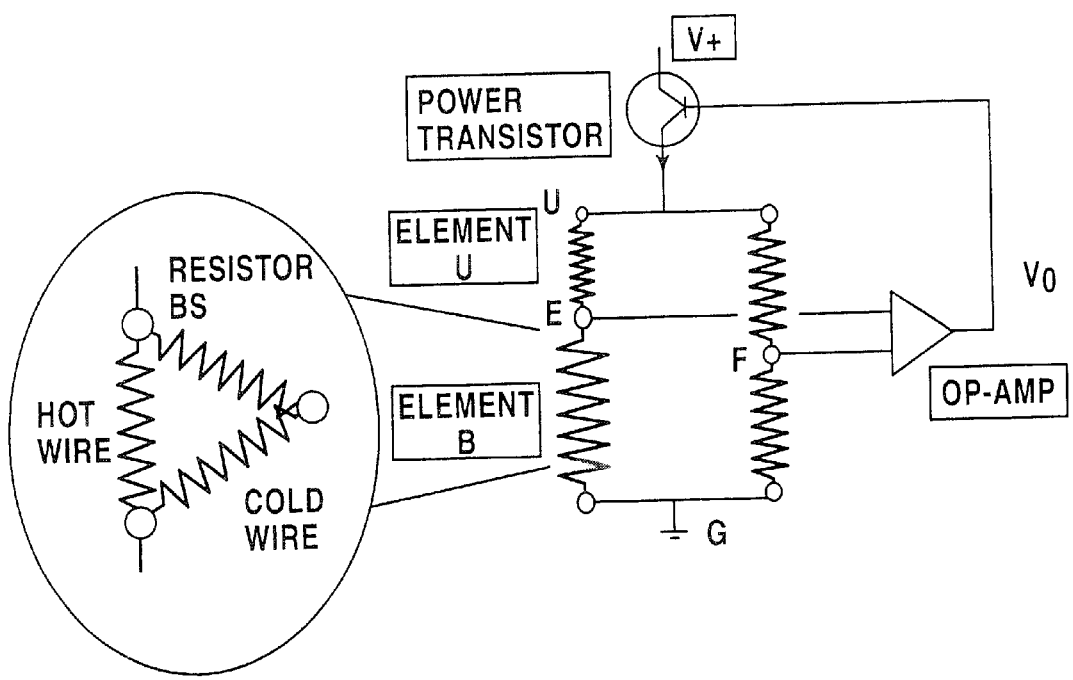
FIG. 5 illustrates a schematic diagram of a wiring circuit used by the control means for simultaneously controlling both heating elements.

FIG. 5 illustrates a schematic diagram of a wiring circuit that can be used by the controller 200 for simultaneously controlling both of the heating elements $252_H$ and $252_C$. Resistor element BS, shown in the close up A of FIG. 5, is provided in the circuit since the heating elements $252_H$ and $252_C$ are maintained at different temperatures (i.e., $T_H$ and $T_C$, where $T_H>T_C$). As such, each component of the circuit has constant resistance except for the heating elements 252. The resistance of the overall equivalent resistor element B, which represents resistor element BS, shown in close up A, is maintained constant by varying the current flowing into the bridge and the voltage at the top of the bridge. Theory suggests that the resistance of element B is constant when the difference of voltage between point E and F is zero, since the resistance of the components on the other legs of the bridge is constant.

Presuming the bridge is balanced, points E and F are at the same voltage and the power transistor supplies only the current necessary to the heating elements $252_H$ and $252_C$ to maintain their respective temperatures. An operational amplifier monitors the voltage difference between point F and point E, $\Delta V_{EF}$. If a change in the gas temperature or gas velocity occurs, the operational amplifier outputs a signal $V_O$ proportional to the difference of voltage $\Delta V_{EF}$. The power transistor reacts to the signal $V_O$ by generating enough current to reach a new equilibrium point. Hence, the control circuit maintains the resistance of element B constant, whatever the boundary conditions are, at least within the power capabilities of the power transistor and the power rating of the resistors in the circuit.

Figure 6:
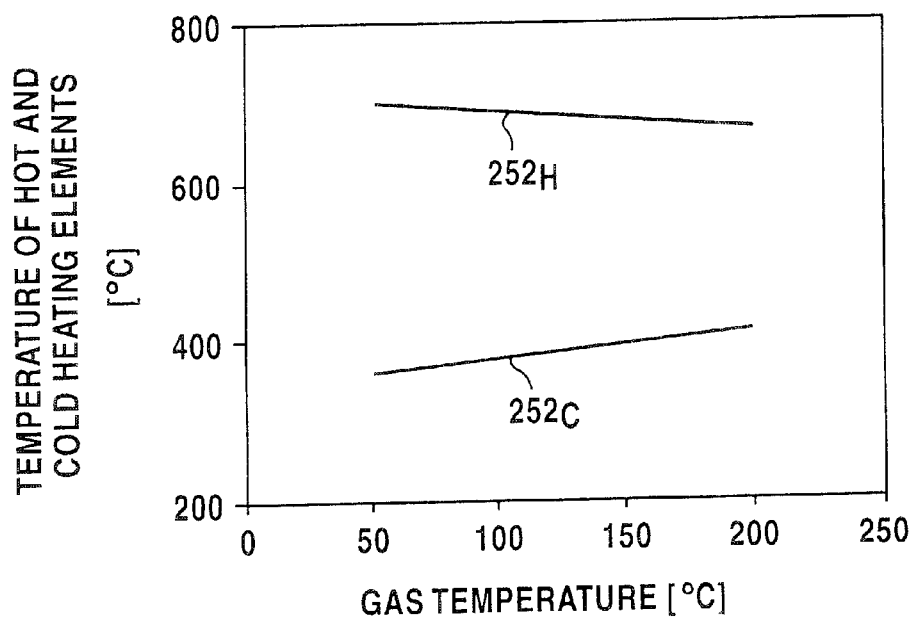
FIG. 6 is a graph illustrating the change in temperature of each heating element relative to the change in the gas temperature.

FIG. 6 illustrates the change in temperature of each heating element $252_H$ and $252_C$ relative to the change in the gas temperature. The resulting temperature of the cold heating element $252_C$ is between the temperature of the hot heating element $252_H$ and the gas temperature because the power ratio for the two heating elements $252_H$ and $252_C$ remains nearly constant. This is a rather significant feature since the ratio of the heat transfer coefficients for the two heating elements $252_H$ and $252_C$ is nearly constant over a wide range of gas temperatures. Further, by keeping the temperature of the cold heating element $252_C$ equally distant from the temperature of the hot heating element $252_H$ and the gas temperature, optimal accuracy in sensor probe 250 measurements is achieved.

In the exemplary second embodiment, the two identical heating elements $252_H$ and $252_C$ comprised of platinum wire are kept above the Leidenfrost transition, at different temperatures from each other, i.e., $T_H$ and $T_C$, where $T_H > T_C$. The energy balance for each platinum wire can be written as:

$$\frac{\Delta V^2}{R} = h \cdot S \cdot (T - T_G) \tag{9}$$

Figure 9:
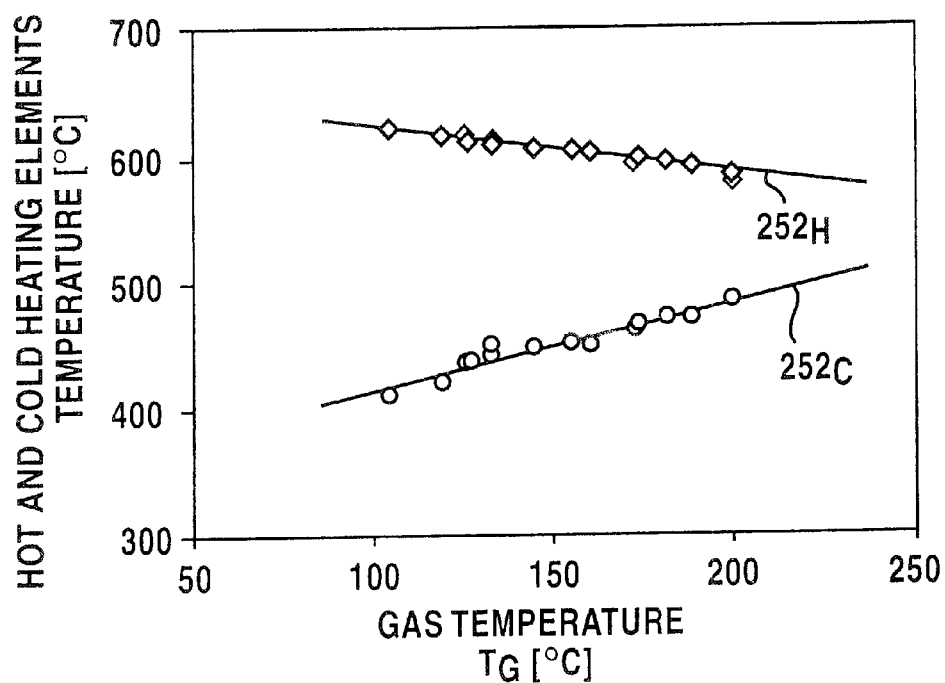
FIG. 9 is a graph illustrating the change in temperature of the hot and cold heating elements of the sensor probe according to the present invention compared to the change in gas temperature.

The arrangement for controlling a double wire component, element B in FIG. 9, is basically a Wheatstone bridge, with an operational amplifier having an output that is proportional to the voltage difference between points E and F. The operational amplifier controls a bipolar gate power transistor so that the ratio of the resistances on the left side of the bridge is constantly equal to the ratio of the resistances on the right side of the bridge. By ensuring that there is no voltage difference between points E and F, the control means 200 maintains the overall resistance of the leg EG to a set value chosen identical to the resistance $R_U$. Also, the resistance of the element BS is chosen equal to $R_U$. To this effect, any control device able to maintain the resistance EG at the constant value $R_U$ is suitable for the operation and control of the probe. Introducing the variable w as the ratio of the voltages across the cold heating element $252_C$ and the resistor element BS, one obtains:

$$\frac{\Delta V_C}{\Delta V_{BS}} = \frac{R_C}{R_U} = w \tag{10}$$

The electrical resistance of a platinum wire is a linear function of its temperature, $R = \alpha \cdot T + \gamma$. If T is measured in Celsius degrees, the coefficients $\alpha$ and $\gamma$ are given respectively by:

$$\alpha = 0.003927 \cdot R_{20} \cdot L \text{ (OHM/}°\text{C.)} \tag{11}$$

$$\gamma = R_{20} \cdot L - 20 \cdot \alpha \text{ (OHM)} \tag{12}$$

where L is the length of the wire expressed in cm and $R_{20}$ is the resistance of platinum per unit length of wire, expressed in ohm/cm, at 20° C. $R_{20}$ depends only on the diameter of the wire. Hence, Equation (10) becomes:

$$\frac{\alpha T_C + \gamma}{R_U} = w \tag{13}$$

Solving Equation (13) with respect to the temperature of the cold heating element $252_C$, the following relationship is obtained:

$$T_C = \frac{R_U \cdot w - \gamma}{\alpha} = \frac{R_U}{\alpha} \cdot w - \frac{\gamma}{\alpha} \tag{14}$$

Similarly, by recalling that the overall resistance of the leg EG is equal to $R_U$, the temperature of the hot heating element $252_H$ can be related to w as follows:

$$T_H = \frac{R_U}{\alpha} \frac{w+1}{w} - \frac{\gamma}{\alpha} \tag{15}$$

by assuming that the heat transfer coefficient is similar for both heating elements $252_H$ and $252_C$, Equation (9), written for both heating elements $252_H$ and $252_C$, yields the following ratio:

$$\frac{w^2}{w+1} \frac{\Delta V_H^2}{\Delta V_C^2} = w + 1 = \frac{T_H - T_G}{T_C - T_G} \tag{16,17}$$

By combining Equations (14), (15) and (17), one may obtain the temperature of the gas as:

$$T_G = \frac{R_U}{\alpha}(w + 1 - 1/w - 1/w^2) - \frac{\gamma}{\alpha} \tag{18}$$

Equivalently, in the range of voltage ratio w between 1 and 1.4, which are suggested as a result of experiments and relevant calculations, the following relation approximates the expression in parenthesis with the necessary accuracy:

$$g(w) = w + 1 - 1/w - 1/w^2 \approx 2.7685w - 2.6569 \tag{19}$$

Consequently, Equation (18) assumes the following form:

$$T_G = 2.7685 \frac{R_U}{\alpha} w - \frac{\gamma + 2.6569 R_U}{\alpha} = A \cdot w + B \tag{20}$$

A number of important observations can be made by the analysis of Equations (14) and (20):

From Equation (14), it is evident that, if the diameter of the heating element 252, if for example it is comprised of a platinum wire, is changed from $d_1$ to $d_2$, keeping constant the length of the wire, the relationship between the temperature of the cold heating element $252_C$ and the voltage ratio does not change if the ratio $R_U/\alpha$ remains the same. This simplifies significantly the design process of the electric circuit. It is possible to maintain the ratio $R_U/\alpha$ constant and the temperature of the heating elements $252_H$ and $252_C$ above the Leidenfrost transition while changing the wire diameter if the resistance $R_U$, and therefore $R_{BS}$, is changed proportionally to the temperature coefficient $\alpha$.

From Equation (20), one may notice that if the ratio $R_U/\alpha$ is not changed while varying the wire diameter, the sensitivity of the sensor probe 250 does not change. It is well known that the sensitivity of a measurement device is proportional to the derivative of the calculated quantity $T_G$ with respect to the measured one w.

Therefore, it is possible to decrease the current flowing into the circuit by simply using a thinner wire, without losing accuracy in the measurement process and remaining above the Leidenfrost transition with both the heating elements $252_H$ and $252_C$. However, other practical restrictions limit the choice to wire diameters that are not too small.

As one can see from Equation (20), the relationship between the gas temperature and the voltage ratio does not depend either on the gas velocity or the presence of the liquid droplets in the hot gas flow, as long as both heating elements $252_H$ and $252_C$ are above the Leidenfrost transition. An increase of the gas velocity translates into an increase of the voltage applied to the bridge in such a way that all the voltages in the bridge rise proportionally to each other. This explains why the ratio w is not affected by changes in the velocity as well as its relationship with the gas temperature. The presence of liquid droplets causes a similar effect on the voltages of the bridge.

Since the functional shown in parenthesis on the right hand side of Equation (20) is almost linear in the range of interest, i.e., 1.1<w<1.4, the gas temperature can be obtained as:

$$T_G = A \cdot w + B \tag{21}$$

The value of the slope A in Equation (21) has been determined experimentally for a variety of conditions. Upon conducting a rather large number of tests, both with and without liquid droplets, the slope A is deemed to be consistent for all tests with a numerical value of approximately 990±110° C. It should be noted that A and B are numerical constants having values that depend on the features of the specific sensor configuration such as, for example only, material, length, width, diameter, and the like, and w is the ratio of the electrical resistance across the second heating element, i.e., $152_C$ and $252_C$, at the lower temperature, i.e., $T_C$, and the electrical resistance across the resistor in series with the second heating element. As such, the constant values for A and B should be calculated based on such characteristics of the sensor, which may vary depending on the intended application of the sensor.

A single point calibration is used to determine the parameter B in Equation (21) and yields:

$$T_G = 990w - 1060 \tag{22}$$

Figure 7:
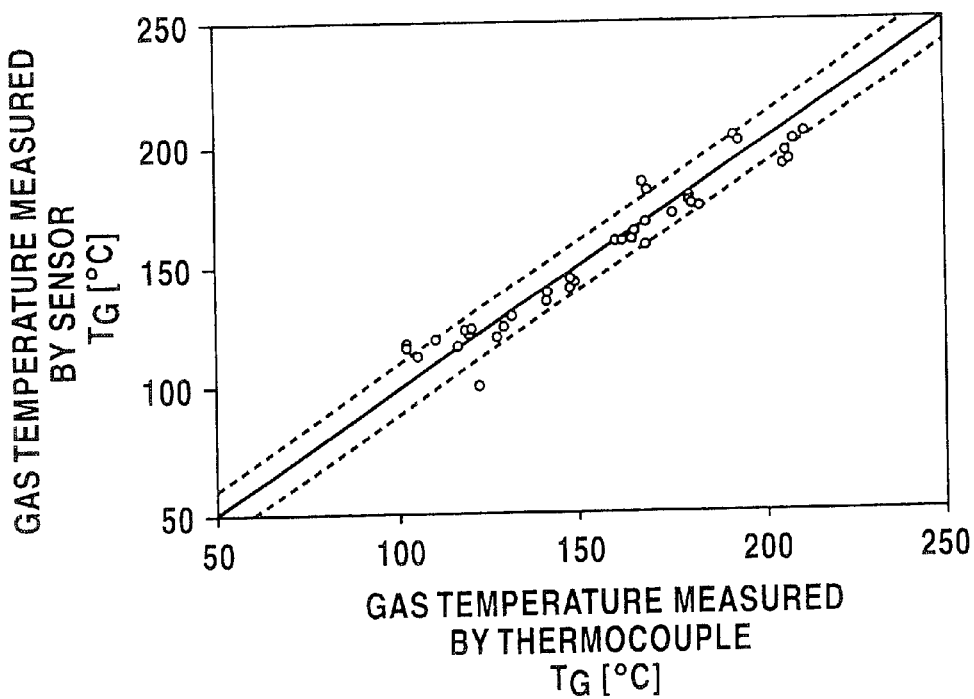
FIG. 7 is a graph illustrating the results of a series of tests using the sensor probe of the present invention compared with using a thermocouple under dry conditions.

FIG. 7 illustrates the results of a series of tests conducted under dry conditions using the sensor probe 250 and comparing the results with those obtained using a K-type thermocouple. The range of gas temperatures investigated is between 100 and 250° C., while the gas velocity is approximately within a 3 to 5 m/s interval. In confirming the effectiveness of the sensor probe 250, FIG. 12 clearly shows that most of the data fall within a band ±10° C. about the exact value with the average error in the range of gas temperature between 100° C. and 200° C. of 7 percent.

Figure 8:
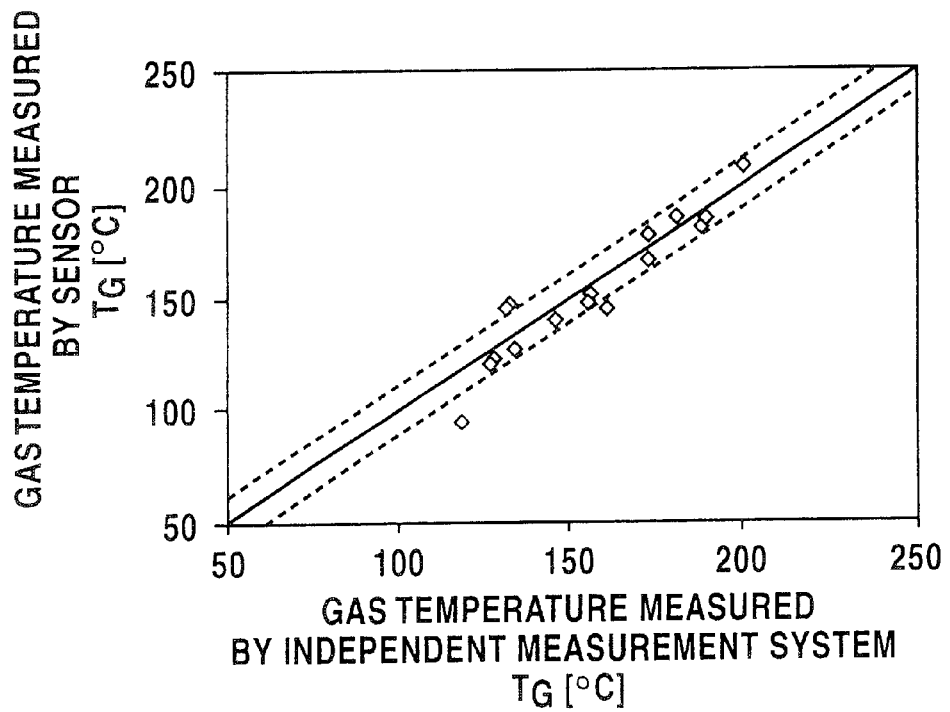
FIG. 8 is a graph illustrating the results of a series of tests using the sensor probe of the present invention compared with the results obtained using the independent measurement system shown in FIGS. 10–13.

FIG. 8 illustrates the results of a second series of tests conducted under wet conditions using Equation (38) based on measurements provided by the sensor probe 250. Eq. (38) is discussed below in further detail. It is important to note that the test results obtained from using the sensor 250 are compared with the gas temperature measurements obtained from the independent measurement system described and illustrated below in conjunction with FIGS. 10–13. As shown, the average error in the range of gas temperature between 100° C. and 200° C. is 5 percent. The results clearly demonstrate the insensitivity of the sensor probe 250 to liquid droplets and the accuracy of the gas temperature readings.

FIG. 9 illustrates the temperature of the hot heating element $252_H$ and the temperature of the cold heating element $252_C$ versus the temperature of the gas. The temperature traces of the heating elements $252_H$ and $252_C$ are linear functions of the resistance of the heating elements $252_H$ and $252_C$. Therefore, the linearity of the temperature trace of the cold heating element $252_C$ confirms the above-provided discussions on measuring the temperature of a hot gas laden with liquid droplets is accurate.

In regards to measuring the liquid volumetric fraction of hot gas laden with liquid droplets, such as water droplets, the liquid droplet volumetric fraction β can be related to the temperature difference between the hot-gas and the temperature $T_W$ detected by a wetted sensor probe 250. The temperature $T_W$ measured by a wetted sensor probe is obtained by the sensor being at a temperature below the Leidenfrost point so the liquid droplets contact the surface of the sensor probe. Consider the steady-state energy balance written for a cylinder immersed in a hot gas stream laden with liquid droplets. All the liquid deposited on the sensor is assumed to evaporate. This is reasonable because the droplets are sparse and the gas temperature high. Therefore, there is little chance for a significant liquid build-up on the sensor leading to run-off or re-entrainment of the liquid in the gaseous stream.

The collection efficiency κ quantifies the number of droplets that will hit the sensor with respect to the total number of droplets that flow through the sensor cross sectional area, A. Under these premises, the energy balance can be written as:

$$\rho_L A U \beta \kappa \Lambda = S h (T_G - T_W) \tag{23}$$

Note that the temperature of the wetted sensor (or wet temperature), $T_W$, can be significantly lower than the hot gas temperature, $T_G$. Introducing the heat transfer correlation for a cylinder in cross-flow for Reynolds number (U·D/$v_G$) ranging between 40 and 1000, one obtains:

$$\beta = 0.52 \pi \frac{\varepsilon \cdot k_G Pr^{0.37}}{\kappa \rho_L v_G^{0.5} \Lambda} \frac{T_G - T_W}{\sqrt{UD}} \tag{24}$$

The parameter ε considers the enhancement of the heat transfer coefficient due to the presence of droplets in the gaseous stream. This parameter is set to 2 for the conditions typical of the applications under consideration. Note that the ratio of the thermal conductivity and the square root of the kinematic viscosity is nearly constant over the range of temperatures of concern. By grouping the numerical values and the physical properties in Eq. (24) into a quantity C, the equation becomes:

$$\beta = \frac{T_G - T_W}{C\sqrt{UD}} \tag{25}$$

The constant C is determined both analytically and experimentally based on the characteristics of the material used for the sensor probe. To determine the value of C analytically, the collection efficiency, κ, is set at 0.96. In the following, C is set to 85 $Ks^{0.5}m^{-1}$ when the liquid volumetric fraction is expressed in parts per million.

With this result, the liquid volumetric fraction can be readily obtained once the wet temperature, the gas temperature, and the gas velocity are measured. As such, one finds that:

$$C = \frac{\chi}{\sqrt{UD}} \quad (26)$$

This relationship provides an independent way to evaluate the evaporative cooling constant. With this approach, the value of C is 86±7 $Ks^{0.5}m^{-1}$.

The diameter of each heating element in the sensor probe 250 influences both the measurement resolution and the collection efficiency κ in opposite ways. Therefore, the choice of the diameter of the cylinder should be carefully optimized in order to minimize the error related to the temperature measurement. The gas velocity U is also necessary to obtain the volumetric fraction.

For identical flow conditions, i.e., U and β constant, the difference of temperature is proportional to the square root of the diameter of the cylinder for each heating element of the sensor probe 250. The experimental results, gathered from several tests with cylinders of different outside diameter provide a slope of 0.47 that confirms the theoretical observations. Therefore, it seems reasonable to have a diameter of the cylinder for each heating element of the sensor probe be as large as possible in order to achieve a good separation between the two temperatures and consequently an increased accuracy in the determination of the liquid volumetric fraction.

However, the diameter of the cylinder for each heating element of the sensor probe affects the collection efficiency and the time response constant of the sensor probe, as well. The collection efficiency provides a measure of the fraction of droplets that cannot avoid the cylindrical obstacle and deposit on the surface. The collection efficiency has been calculated for a wide range of the inertia parameter Z. The parameter Z is defined as the Reynolds number (Re) for the wetted sensor times the square of the ratio of the droplet diameter and wetted sensor diameter times the ratio of the water and air densities. The results have been fitted analytically by the following correlation:

$$\kappa = \frac{Z^{1.08}}{Z^{1.08} + 8.80} - 0.04 \quad (27)$$

After comparing the collection efficiency and the diameter of the cylinder for each heating element of the sensor probe 250, it should be noted that the collection efficiency approaches an asymptotic value of 0.97 for small sensor diameters and the collection efficiency decreases if the diameter of the cylinder increases.

The time constant of the wet sensor probe can be obtained from a transient lump-capacity energy equation written as:

$$\rho_S c_S V_S \frac{dT_S}{dt} = h \cdot S(T_G - T_S) \quad (28)$$

By introducing a heat transfer correlation, the solution of Equation (28) yields a time constant given by:

$$\tau = \frac{\rho_S c_S V_G^{0.5}}{2.08 k_G U^{0.5} Pr^{0.37}} d^{1.5} \quad (29)$$

Experimental results suggest an exponent of 1.58 which is in reasonable agreement with the value of 1.5 suggested by the theory. As such, the time constant constraint favors small sensor diameters if a fast response time is desirable. On the basis of the results previously obtained, the optimal diameter of the wet sensor can be chosen so that the time response is compatible with the sensor of this application. Also, the restriction to remain in the asymptotic region of the droplet collection efficiency curve is desirable, together with the best measurement accuracy possible. Note that dealing with constant collection efficiency greatly simplifies the implementation of the technique.

Therefore, the liquid volumetric fraction for liquid droplets is therefore simplified as:

$$\beta = (0.012 \pm 0.001)(T_G - T_W)/(UD)^{1/2} \quad (30)$$

Several experiments were performed and the measurements of the liquid volumetric fraction obtained with an optical method were compared with those obtained from Equation (30), measuring $T_G$ with the sensor probe 250 and $T_W$ with the wet temperature sensor. Using the sensor probe 250 provides a more precise value of the liquid volumetric fraction than that obtained with the optical method. Furthermore, while the optical method requires steady state conditions and is based on the examination of a statistically relevant number of picture frames, the sensor probe 250 is merely limited by the response time of the sensor probe.

As stated in regards to the first embodiment of the sensor probe 150, the particular components of the controller 200 is not pertinent to an understanding of the controller. However, the controller 200 should be able to perform several functions in addition to being able to control two heating elements at the same time. For example, the controller 200 should maintain, in any condition, the resistance of element EG constant and equal to the resistance of element $R_U$. Aside from this, the controller 200 should allow for a fast and reliable acquisition of the sensor outputs.

In accordance with an embodiment of the present invention, the controller 200 should also be capable of providing feedback to control the temperature of the heating elements and to maintain the feedback above predetermined minimum values. The controller 200 should provide fixed-point arithmetic to convert incoming voltages to temperature.

In accordance with an embodiment of the present invention, an independent measurement system was used to validate the measurements obtained with the sensor probe. FIGS. 10–13 illustrate an example of such a measurement system. It should be noted that the illustrated system is merely exemplary and that the system may have numerous variations in structure so long as the below discussed theory is applicable.

Figure 10:
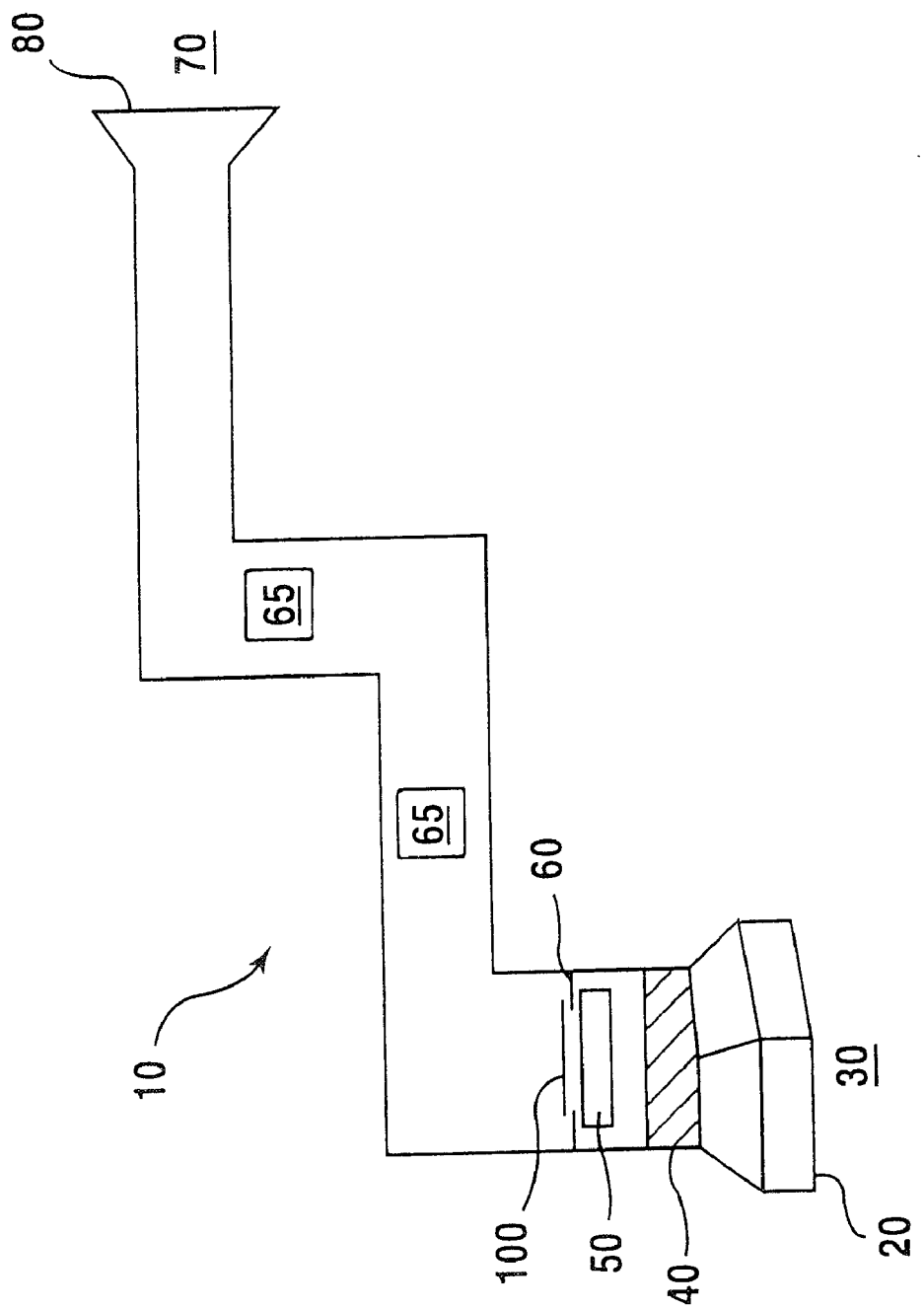
FIG. 10 is a schematic diagram of a once through circuit duct system of an independent measurement system in which a hot gas flow is established to measure the response of a sensor probe according to this invention.

FIG. 10 illustrates a schematic diagram of a once through circuit duct system 10 in which a hot gas flow is established to measure the thermal response of a simulated sprinkler link probe immersed therein. For example, the system 10 may include a square duct, such as a duct having a 0.61 m×0.61 m cross-section, wherein the dimensions are merely exemplary, through which a steady air flow is induced by a blower 70, such as a fan, positioned near the outlet 80.

Air entering the inlet 20 is heated by a heat source 30, such as, for example only, a 70 kW natural gas burner, that warms up the air at the inlet. The hot gas proceeds through a honeycomb structure 40 comprising, for example only, tightly packed steel wool, positioned immediately adjacent the inlet 20 to obtain a uniform velocity and temperature of the hot gas. It is within the scope of this invention to have the honeycomb structure 40 comprise any other suitable material so long as the velocity and temperature of the hot gas passing through the structure is uniform upon exiting.

Figure 11:
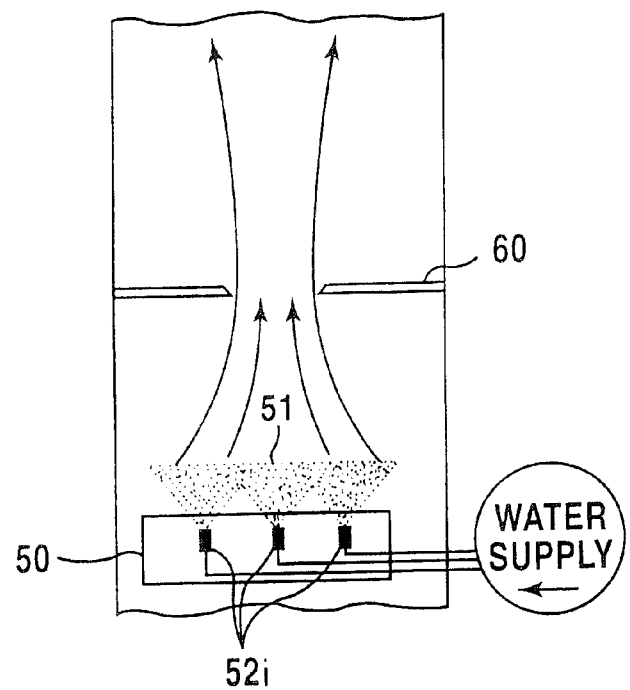
FIG. 11 is a schematic diagram showing the uniform flow of hot gas passing through a finely atomized liquid spray after passing through a honeycomb structure of the system shown in FIG. 10.

As shown in FIG. 11, after passing through the honeycomb structure 40, the hot gas enters a plenum 50 having a plurality of spray nozzles 52*i*, wherein i=2, 3, 4, . . . n, that add liquid to the hot gas. It is within the scope of this invention to have n equal the number of spray nozzles necessary to provide the needed spray of liquid droplets. Furthermore, it should be understood that the spray nozzles are to be chosen so as to provide the desired amount of liquid droplets having a predetermined droplet size distribution.

The flow of the hot gas laden with liquid droplets 51 is then accelerated through an orifice 60, the geometry of the orifice being any suitable geometric shape, such as, for example only, circular, rectangular, triangular, trapezoidal, and the like. The actual geometry of the orifice is not of critical importance so long as the flow of the hot gas emerging therefrom is uniform. The cross-sectional area of the orifice 60 may be, for example only, 0.25 m in diameter and located approximately 0.5 m downstream of the spray nozzles 52*i*.

Figure 12:
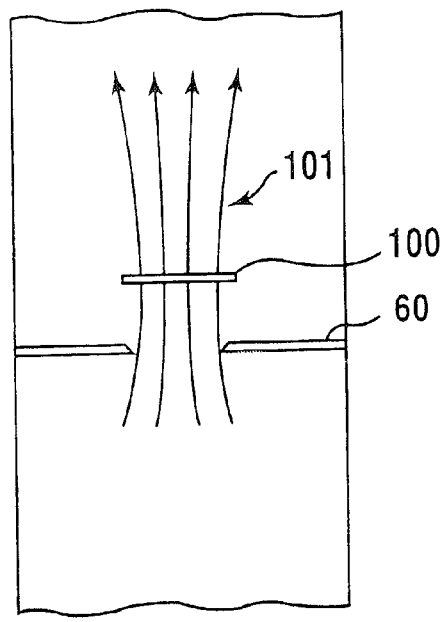
FIG. 12 illustrates the location of the vena contracta and test section in the duct system shown in FIG. 10.

As shown in FIG. 12, the test section 100 is located downstream of the orifice 60 in the vena contracta and the velocity field in the test section 60 is one-dimensional. A plurality of thermocouples are positioned downstream of the orifice 60 to provide a description of the evolution of the temperature of the hot gas. Although different configurations of the duct system 10 will yield different results, within the cross-section of the illustrated system, the temperature variation detected by plurality of thermocouples was determined not to exceed 8° C. in both gas and gas-liquid conditions. Furthermore, a plurality of thermocouples, such as, for example only, type K, ±2° C., are placed inside the system 10, both before and after the test section 100 so as to measure the gas temperature distribution along the duct and monitor the conditions during the experiment. The hot gas flow is cooled by the heat transferring to the walls of the duct system and by mixing cold air drawn into the system through secondary inlets 65, as shown in FIG. 10.

With conventional methods and devices, temperature measurements, as well as determination of other properties, of a hot gas laden with liquid droplets are significantly affected by evaporative cooling as liquid droplets impact, for example, the temperature sensor, or other device being used to measure the property, and evaporate on its surface. The following description provides a novel approach to the measurement of the temperature and other properties of the hot gas. It should be noted that one aspect of the present invention is that the sensor probe is maintained at temperatures exceeding the Leidenfrost transition so as to be insensitive to the presence of the liquid droplets in the hot gas.

Figure 13:
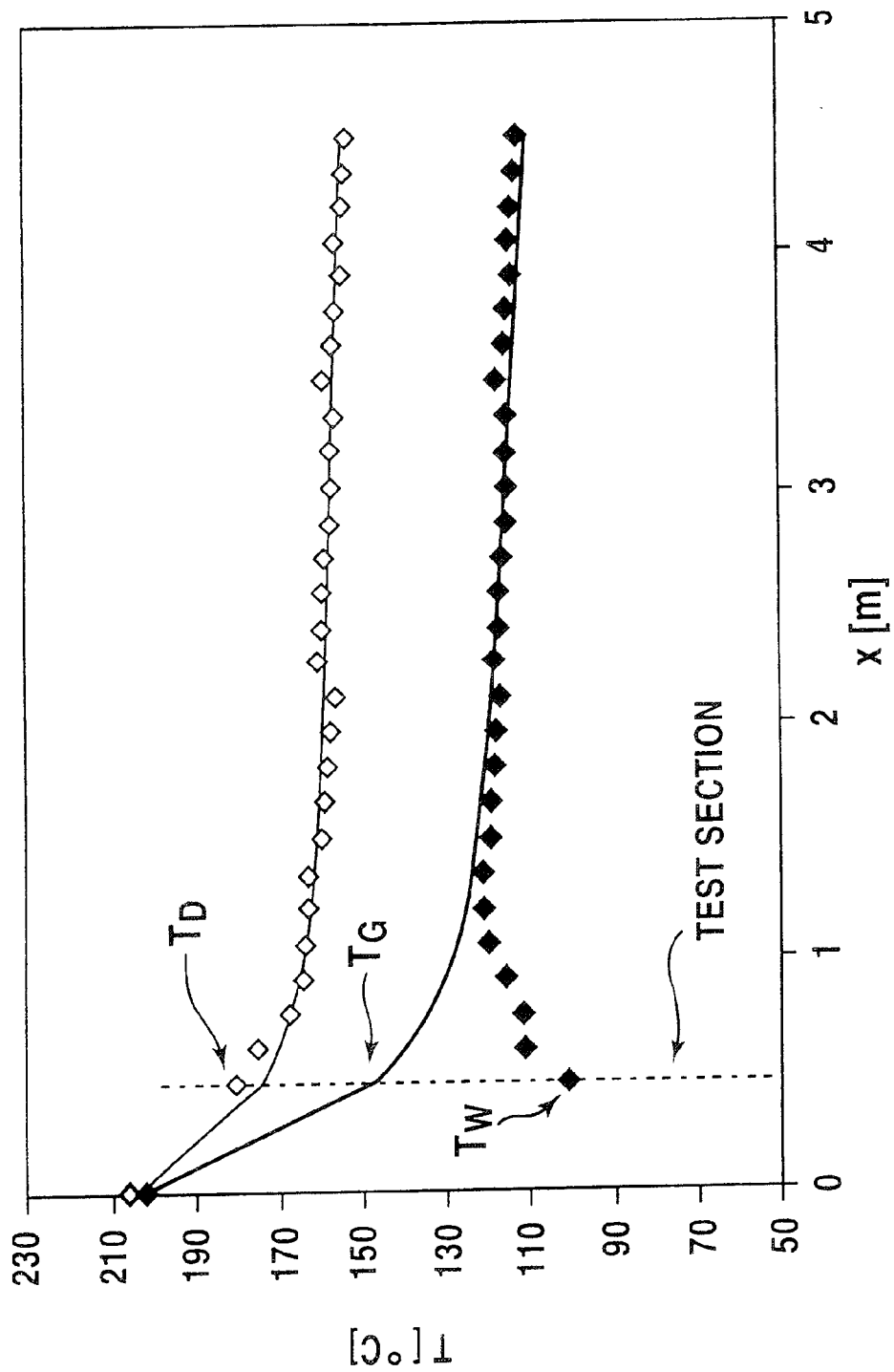
FIG. 13 is a graph illustrating temperature distribution for dry and wet conditions.

FIG. 13 illustrates a typical temperature distribution for probes in both dry and wet conditions performed in accordance with the test device described further below. $T_D$ is a curve of the temperature of the gas as measured in a dry environment, with the data points indicated. $T_G$ is the estimate of the gas temperature in wet conditions. $T_W$ presents the data for the temperature detected by the conventional probe in wet conditions. A comparison between the values of the temperature measured at a test section after which liquid droplets have been introduced clearly shows the effect of the evaporative cooling in wet conditions on the wet probe.

It is worth noting that, due to the heat losses to the external environment, the temperature drops as the flow proceeds downstream of the introduction of the gas. Furthermore, approximately 2 m downstream the test section indicated in the graph shown in FIG. 13, the slope of the temperature distribution for the wet condition nearly equals the slope for the temperature distribution for the dry condition, which is indicative of the liquid being completely evaporated and that the temperature being affected only by the heat losses to the environment. The difference in temperature T ° C. between the temperature profiles of the dry and wet conditions $T_D$ and $T_W$, respectively, a considerable distance from the orifice of introduction of the gas can be related to the heat required to vaporize the liquid droplets To determine the gas temperature $T_G$ between the sprays and the location of the complete evaporation of the liquid, some information concerning the rate of vaporization of the droplets is needed. Consider the energy balance written for the air flow as:

$$\rho_G \dot{V}_G c_G (T_D - T_G) = \rho_L \dot{V}_G (\beta_0 - \beta) \Lambda \tag{3}$$

Consider the asymptotic temperature difference, $\Delta T$, between the two traces in FIG. 13, which is associated with the sensible heat removed from the air in order to vaporize the droplets. This difference can be expressed in the following form:

$$\Delta T = \frac{\rho_L \dot{V}_G \cdot \beta_0 \cdot \Lambda}{\rho_L \dot{V}_G c_G} \tag{32}$$

With Eq. (32), Eq. (31) can be simplified as:

$$T_D - T_G = \Delta T [1 - f(x)] \tag{33}$$

where the function f(x) links the initial volumetric fraction to its evolution along the duct.

The energy balance written for a thermocouple wetted by liquid droplets yields a relation of proportionality between the convective heat input to the thermocouple and the latent heat associated with the vaporization of the droplets that impact over the surface of the thermocouple. For the purpose of measuring the gas temperature $T_G$, a simple form of the energy balance is given as:

$$h(T_G - T_W) \propto \rho_L U \beta \Lambda \tag{34}$$

Considering the volumetric fraction evolution during the evaporation process, Eq. (34) can be rearranged as:

$$T_G - T_W = \chi \beta_0 f(x) \tag{35}$$

By adding Eq. (33) and Eq. (35), one finds that the functional f(x) can be expressed in the following form:

$$f(x) = \frac{T_D - T_W - \Delta T}{\chi \beta_0 - \Delta T} \tag{36}$$

It should be noted that f(x) must be equal to 1 at the spray nozzles location and equal to zero for x greater or equal to $x_E$, a point at which all the liquid droplets are evaporated. A reasonable representation of the data is obtained as:

$$f(x) = \begin{cases} \left(1 - \frac{x}{x_E}\right)^\lambda & x \leq x_E \\ 0 & x > x_E \end{cases} \tag{37}$$

It follows that the interpolation describing the gas temperature $T_G$ is given by substituting Eq. (37) into Eq. (33) to yield:

$$T_G = T_D - \Delta T \left[ 1 - \left(1 - \frac{x}{x_E}\right)^\lambda \right] \tag{38}$$

the temperature in dry conditions $T_D$ is represented with an exponential fit of the available data in the following form:

$$T_D = (T_0 - D)e^{-\alpha x} + Bx + D \tag{39}$$

The constant B represents the slope of the trace on the right hand side due to the heat transfer losses to the ambient. It is reasonable to presume that this approach provides a good representation of the hot gas temperature trend. In particular, the intersection of this curve with the vertical dashed line in FIG. 1 provides the hot gas temperature at the test section point for liquid droplets introduced into a hot gas under test conditions described further below. As one may notice from the plot, the evaporative cooling reduces the thermocouple reading of the wet probe by some 50° C. with respect to the estimated gas temperature $T_G$.

It should also be noted that in the independent measurement system being described, the test section 100 is illuminated by a laser, such as, for example only, a 600 mW Argon-ion laser sheet. However, it should be noted that any suitable illumination device can be used. The velocity measurements in the cross-section are obtained with a particle tracking velocimetry technique that yields uncertainty in the velocity measurements of approximately 10 percent.

As the volumetric mean diameter of the droplets is less than 100 μm, the terminal velocity is smaller than approximately 0.14 m/s. Since the gas velocities are in excess of 3.5 m/s, the difference between the droplet and gas velocities introduces an error of less than 4 percent in the gas velocity measurement.

While there has been illustrated and described what is at present considered to be preferred embodiments of the present invention, it will be understood by those skilled in the art that various changes and modifications may be made, and equivalents may be substituted for elements thereof without departing from the true scope of the invention.

Figure 14:
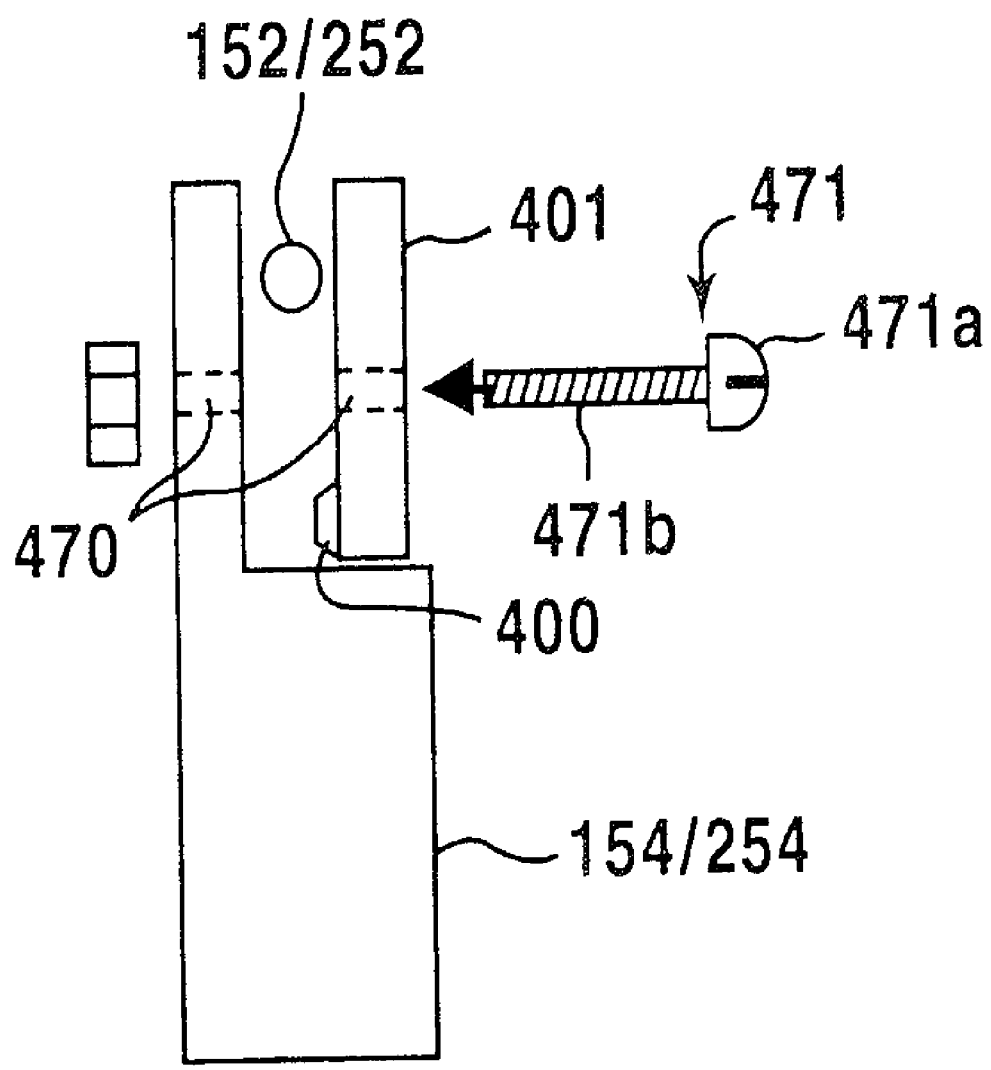
FIG. 14 illustrates an alternate manner of connecting the heating elements of the sensor probe to the rods of the sensor probe.

For example, as shown in FIG. 14, a terminal 400 may be provided to support the heating elements 152 and 252 held by the rods 154 and 254. In this arrangement, the heating element 152 of 252 is placed between a clamp 401 and the rod 154 or 254. Each rod 154 or 254 has a bore 470 formed therein that is sized and configured to receive a fastening device 471, which is shown as a screw, but can be any known or later developed suitable device. When the threaded portion 471*b* of the fastening device 471 is threadably inserted into the bore 470 of the rod 154 or 254, the head portion 471*a* of the fastening device 471 secures the clamp in place and the terminal 400 prevents the heating element 152 or 252 from being crushed. Thus, the mounting of the heating element 152 or 252 onto the rod 154 or 254 is easier and a better match between the copper rods and the platinum heating elements are achieved, resulting in a lower resistance of contact.

In addition, many other modifications may be made to adapt a particular situation or material to the teachings of the invention without departing from the scope thereof. For example, although the above-provided discussion of the present invention discussed application of the sensor probe in application with a simulated sprinkler link, it is in no way intended to limit the scope of the applications of the present invention. In particular, it is envisioned that the sensor probe includes applications in numerous fields.

Specifically, in aerospace engineering, the sensor probe can easily find applications in the cooling process of turbomachinery blades and in the study of fuel evaporation within the combustion chamber. Likewise, in the field of automotive engineering, the sensor probe can be used in the investigation of the fuel evaporation process between the point of injection and the engine cylinder inlet. Furthermore, in the chemical/process industry and laboratories, further applications can be found in any process where a liquid is entrained and carried by a gas flow, such as cooling towers and multiple phases mixing. Therefore, it is intended that this invention not be limited to the particular embodiment or application disclosed herein, but will include all embodiments and applications within the spirit and scope of the disclosure.

GLOSSARY

Λ=latent heat of vaporization of water

A, B=numerical constants having values that depend upon configuration of the sensor probes b=an exponent less than one β=a liquid volumetric fraction C=a constant $C_G$=evaporative cooling parameter for gas $c_S$=specific heat d=cylinder diameter D=an outer diameter of the wetted sensor probe ϵ=a parameter that considers the enhancement of the heat transfer coefficient due to the presence of droplets in the gaseous stream F=a coefficient that depends on the ratio of the heat transfer coefficients f(x)=a function that links the initial volumetric fraction to its evolution along the duct $H_C$=the heat transfer coefficient for the cold heating element $H_H$=the heat transfer coefficient for the hot heating element $i_C$=the current in the cold heating element $i_H$=the current in the hot heating element κ=the liquid droplet collection efficiency for wet sensor $k_G$=gas thermal conductivity l=length of wire expressed in cm Pr=Prandtl number $\rho_L$=density of liquid $\rho_S$=density of solid $Q_C$=the power to maintain the cold heating element at the cold element predetermined temperature $Q_H$=the power to maintain the hot heating element at the hot element predetermined temperature $R_{20}$=resistance of platinum per unit length of wire, expressed in ohm/cm, at 20° C.

$R_C$=the resistance in the cold heating element $R_H$=the resistance in the hot heating element $R_U$=the resistance of leg EG in FIG. 5

S=heat transfer surface, m²

$T_C$=the temperature of the cold heating element $T_H$=the temperature of the hot heating element $T_G$=temperature of gas $T_S$=temperature of heat transfer surface $T_W$=a temperature measured by a wetted sensor $\Delta V_{BS}$=voltage change across resistor element BS in FIG. 5

ΔV$_C$=change in voltage across the cold heating element
ΔV$_{EF}$=voltage difference between points E and F in FIG. 5
ν$_G$=kinematic viscosity of gas
V$_G$=volumetric
V$_S$=volume of solid
ΔV$_H$=change in voltage across the hot heating element
U=a velocity of the hot gas laden with liquid droplets
w=the ratio of an electrical resistance across the second heating element at the second temperature to an electrical resistance across a resistor of the controller that is in series with the second heating element
χ=parameter in equation 5
x$_E$=a point at which all the liquid droplets are evaporated
λ=exponent of the water volumetric fraction evolution
Z=inertia parameter

We claim:

1. A sensor probe that measures characteristics of a gas laden with liquid droplets, the sensor probe comprising:
   at least two heating elements, each heating element is connected in series with an insulator,
   a support frame, wherein the insulator connected to each heating element is connected to the support;
   a controller that controls operation parameters of each of the heating elements, the support frame being connected to the controller;
   wherein temperature is an operation parameter of the heating elements controlled by the controller,
   wherein a first heating element of the at least two heating elements is configured to be maintained at a first temperature and a second heating element of the at least two heating elements is configured to be maintained at a second temperature that is less than the first temperature,
   wherein the first and second temperatures are above a Leidenfrost transition temperature for the liquid at atmospheric conditions and a temperature of the gas laden within the liquid droplets is determined by a relationship between a function of the first and second temperatures of the first and second heating elements positioned in a flow of the gas having a velocity orthogonal to a longitudinal axes of the first and second heating elements and a ratio of power supplied to the first and second heating elements by the controller, the relationship is not affected by the velocity of the gas flow and the presence of the liquid droplets in the gas flow.

2. The sensor probe according to claim 1, wherein the liquid is water.

3. The sensor probe according to claim 1, wherein the function of the first and second temperatures of the first and second heating elements and ratio of power supplied to the first and second heating elements provides the temperature of the gas laden with the droplets of the liquid based on the following relationship:

$$T_G = A \cdot w + B$$

wherein T$_G$ is the temperature of the gas, a and b are numerical constants having values dependent upon a configuration of the sensor probe and w is a ratio of an electrical resistance across the second heating element at the second temperature and an electrical resistance across a resistor that is in series with the second heating element.

4. A method of measuring characteristics of a gas laden with liquid droplets using a sensor probe having at least two heating elements, each heating element being connected in series with an insulator and a support frame, a controller controls the temperature of each of the heating elements and is connected to the support frame, wherein a first heating element of the at least two heating elements is configured to be maintained at a first temperature and a second heating element of the at least two heating elements is configured to be maintained at a second temperature that is less than the first temperature, the method comprising the following steps of:
   positioning the first and second heating elements in a flow of gas laden with droplets of the liquid, wherein the flow of gas has a velocity that is orthogonal to a longitudinal axes of the first and second heating elements;
   supplying power from the controller to the first and second heating elements
   maintaining the first and second temperatures above a Leidenfrost transition temperature for the liquid at atmospheric conditions; and
   determining a temperature of the gas laden within the droplets of the liquid based on a relationship between a function of the first and second temperatures of the first and second heating elements and the power supplied to the first and second heating elements,
   wherein the relationship is not affected by the velocity of the gas flow and the presence of the droplets of the liquid in the gas flow.

5. The method according to claim 4, comprising the additional step of determining the temperature of the gas laden with the liquid droplets based on the following relationship:

$$T_G = A \cdot w + B$$

wherein T$_g$ is the temperature of the gas, a and b are numerical constants having values dependent upon a configuration of the sensor probe, and w is the ratio of an electrical resistance across the second heating element at the second temperature and an electrical resistance across a resistor that is in series with the second heating element.

6. The method according to claim 4, comprising the step of determining a liquid volumetric fraction of the gas laden based on the following relationship:

$$\beta = (0.012 \pm 0.001)(T_G - T_W)/(U \cdot D)^{1/2}$$

wherein β represents a liquid volumetric fraction, T$_G$ is a temperature of the gas laden with the liquid droplets, T$_w$ is a temperature measured by a wetted sensor, U is a velocity of the gas laden with the liquid droplets, and D is an outer diameter of the wetted sensor.

7. The method according to claim 4, wherein the Leidenfrost transition for the liquid droplets is in a range between 300–350° C. at atmospheric conditions.

8. The method according to claim 4, comprising the step of the controller controlling the first and second heating elements simultaneously.

9. The method according to claim 4, comprising the step of arranging the first and second heating elements parallel relative to each other.

10. The method according to claim 4, comprising the step of arranging the first and second heating elements to be coaxial relative to each other.

11. A sensor probe that measures characteristics of a gas laden with liquid droplets, the sensor probe comprising:

at least two heating elements, each heating element being connected in series with an insulator, support means for supporting the at least two heating elements and insulator, wherein the insulator is connected to the support means;

control means for controlling operation parameters of each of the heating elements, the support means being connected to the control means;

wherein temperature is an operation parameter of the heating elements controlled by the control means, wherein a first heating element of the at least two heating elements is configured to be maintained at a first temperature and a second heating element of the at least two heating elements is configured to be maintained at a second temperature that is less than the first temperature, wherein the first and second temperatures are above a Leidenfrost transition temperature for liquid at atmospheric conditions and a temperature of the gas laden within the liquid droplets is determined by a relationship between a function of the first and second temperatures of the first and second heating elements positioned in a flow of the gas having a velocity orthogonal to a longitudinal axes of the first and second heating elements and a